United States Patent [19]

Nielsen

[11] Patent Number: 5,733,764
[45] Date of Patent: Mar. 31, 1998

[54] METHOD FOR PURIFICATION OF AN AQUEOUS ENZYME SOLUTION

[75] Inventor: Niels-Viktor Nielsen, Kr. Såby, Denmark

[73] Assignee: Novo Nordisk A/S, Bagsvaerd, Denmark

[21] Appl. No.: 347,470

[22] PCT Filed: Jul. 6, 1993

[86] PCT No.: PCT/DK93/00229

§ 371 Date: Dec. 8, 1994

§ 102(e) Date: Dec. 8, 1994

[87] PCT Pub. No.: WO94/01537

PCT Pub. Date: Jan. 20, 1994

[30] Foreign Application Priority Data

Jul. 10, 1992 [DK] Denmark .................. 0910/92

[51] Int. Cl.[6] .................................................. C12N 9/00
[52] U.S. Cl. .................. 435/183; 435/188; 435/814; 435/816; 210/696

[58] Field of Search .................................. 435/188, 183, 435/187, 814, 816, 174, 176; 210/696

[56] References Cited

U.S. PATENT DOCUMENTS

| | | | |
|---|---|---|---|
| 3,664,926 | 5/1972 | Grabner et al. | 435/229 |
| 3,795,586 | 3/1974 | Ziffer . | |
| 4,237,231 | 12/1980 | Jackson et al. | 435/234 |
| 4,711,739 | 12/1987 | Kandathil | 252/139 |
| 4,994,200 | 2/1991 | Disch et al. | 252/106 |
| 5,385,837 | 1/1995 | Boyer et al. | 435/221 |

FOREIGN PATENT DOCUMENTS

WO 90/13632  11/1990  WIPO .

*Primary Examiner*—Leon B. Lankford, Jr.
*Attorney, Agent, or Firm*—Steve T. Zelson, Esq.; Valeta Gregg, Esq.

[57] ABSTRACT

Particular enzymes are precipitated from a mixture of proteins by the simultaneous addition of a soluble aluminate and acid. The pH of the mixture is at least one pH unit from the isoelectric point of the particular enzyme.

12 Claims, No Drawings

METHOD FOR PURIFICATION OF AN AQUEOUS ENZYME SOLUTION

CROSS-REFERENCE TO RELATED APPLICATIONS

This application is a 371 of PCT/DK93/00229 filed Jul. 6, 1993, published as WO94/01537 Jan. 20, 1994 which is incorporated herein by reference.

In order to purify or concentrate an aqueous enzyme solution, especially an enzymatic fermentation broth, different purification methods are known in the art. Examples are salting-out and treatment with activated carbon. However, the selectivity, with which these purification methods separate enzymes from carbohydrates, non enzymatic proteins, colored compounds, and other impurities is open to improvement.

Thus, the purpose of the invention is the provision of a method for purification of an aqueous enzyme solution by means of which the enzymes can be effectively separated from carbohydrates, non enzymatic proteins, colored compounds, and other impurities. Usual sources of aqueous enzyme solutions are fermentation broths or filtered fermentation broths.

The method for purification of an aqueous enzyme solution according to the invention is characterized by the fact that a soluble aluminate is added to the aqueous enzyme solution, and that simultaneously an acid is added in such amounts that the pH-value of the solution is maintained between 4 and 10 and that the pH-value differs at least 1 pH unit from the isoelectric point of the enzyme to be purified, whereby the soluble aluminate is added to the solution in an amount between a maximum amount, which will precipitate no more than a negligible amount of enzyme and a minimal amount, which will leave no more than a negligible amount of impurities, mainly carbohydrates, in solution, and that the supernatant subsequently is separated from the precipitate, which is discarded.

It has been found that the precipitation process proceeds in the most efficient manner at lower pH-values. However, most enzymes exhibit low stability at low pH-values. Thus, a compromise pH-value with a reasonably efficient process and a reasonably good enzyme stability has to be chosen.

According to the invention it surprisingly has been found that the "window", i.e. the interval of added aluminate, in which practically no enzymes are precipitated and practically all impurities are precipitated, is larger than for other precipitating agents, if the precipitation is carried out by means of the method according to the invention.

It is to be understood that the addition of the soluble aluminate to the pH-adjusted enzyme solution with subsequent precipitation of aluminum hydroxide will change the pH, but that according to the invention the pH-value will be readjusted with formic acid, if the changed pH-value should not fulfil the above indicated conditions, i.e. if the changed pH-value should not lie in the interval between 4 and 10, and if it should not differ at least 1 pH unit from the isoelectric point of the enzyme to be purified.

In this specification with claims "a soluble aluminate" means an aluminate, the solubility in aqueous medium of which is above 100 g/l of solution at a temperature of 25° C. An example is sodium aluminate.

The maximum amount of aluminate, which will precipitate no more than a negligible amount of enzyme is dependent upon the kind and the concentration of the enzyme, and it will normally be around 5% w/w aluminate in regard to the solution.

The minimal amount of aluminate, which will precipitate no more than a negligible amount of impurities, mainly carbohydrates, is dependent upon the kind and concentration of the impurities, and it will normally be around 0.5% w/w in regard to the solution.

A few enzymes will tend to precipitate to a certain degree already with addition of the soluble aluminate in an amount of 0.8% aluminate in regard to the solution, and such enzymes are not very well suited for this invention.

U.S. Pat. No. 3,795,586 describes a purification method for enzymes, in which aluminum hydroxide and other insoluble compounds are precipiated in situ. However, in all examples, in which aluminum hydroxide is formed, aluminum sulphate was used, and it has been found that a much more effective separation of enzyme from impurities can be obtained by means of aluminate in combination with an acid, according to the invention.

In WO 91/09943, page 8, lines 11–13 it is indicated that $NaAlO_2$ is added to a fermentation broth in an amount of 4 g of $NaAlO_2$/l of fermentation broth during the flocculation step. An addition of $NaAlO_2$ in a concentration of that size will not precipitate any dissolved material, but only flocculate already existing particles. Thus, this concentration of $NaAlO_2$ is smaller than the minimum amount of aluminate indicated in claim 1.

A preferred embodiment of the method according to the invention comprises that the mixture comprising soluble aluminate, aqueous enzyme solution and acid also contains a water miscible solvent, preferably an alcohol. It has been found that the use of relatively high concentrations of aluminate (e.g. more than around 0.8%, calculated as Al) in some cases can generate substantial losses of enzymes during the initial flocculation, due to adsorption of the enzyme on the aluminum containing flocs. This embodiment of the invention, however, can prevent these substantial losses. The alcohol is usually added prior to the flocculation, and this addition will not change the positive effect of the aluminate, and nor will it harm the separation of the supernatant from the precipitate.

A preferred embodiment of the method according to the invention comprises that the alcohol is glycerol or a glycol. It has been found that glycerol or glycols are well suited alcohols for prevention of the above indicated substantial losses of enzyme.

A preferred embodiment of the method according to the invention comprises that the alcohol is present in the mixture in an amount of between 20 and 80% w/w. It has been found that the interval 20–80% w/w of alcohol is the optimal interval for the most efficient prevention of the substantial losses of enzymes.

A preferred embodiment of the method according to the invention comprises that the acid is formic acid. It has been found that formic acid provides a more selective separation than other acids.

A preferred embodiment of the method according to the invention comprises that the pH-value of the solution is maintained between 5 and 8. This pH interval is optimal for most enzymes.

A preferred embodiment of the method according to the invention comprises that the soluble aluminate is sodium aluminate. Sodium aluminate is the cheapest aluminate and is commercially available.

A preferred embodiment of the method according to the invention comprises that the maximum amount of aluminate is between 2 and 3% w/w of the solution, calculated as Al.

and that the minimal amount is between 0.3 and 1% w/w of the solution, calculated as Al. These values for the maximum and minumum additions of aluminate provide an efficient separation for most enzymes.

A preferred embodiment of the method according to the invention comprises that the supernatant is separated from the precipitate by centrifugation or filtration. These are the most efficient and simple methods of separation.

A preferred embodiment of the method according to the invention comprises that a flocculation agent is added after addition of the acid and the aluminate, but before the separation of the supernatant and the precipitate, and that the flocculation agent is a cationic and/or anionic flocculation agent. By use of these flocculation agents an even better separation is provided.

The method according to the invention will be illustrated by the following examples.

EXAMPLE 1

Savinase® is fermented according to U.S. Pat. No. 3,723,250.

To 1 l of fermentation broth is added:

| Water | 1.5 l |
|---|---|
| Calcium chloride dihydrate | 10 g |
| Sodium aluminate | 40 — |
| Formic acid | approx. 40 — | pH is kept in the interval of 5.5–6.0 by control of the dosage of formic acid.

| Rohafloc KF 785 | approx. | 300 mg |
|---|---|---|
| Superfloc A 130 | — | 150 — |

The supernatant is separated from the precipitate by centrifugation.

Rohafloc KF 785 is a cationic flocculating agent from R öhm, and Superfloc A 130 is an anionic flocculating agent from American Cyanamid.

EXAMPLE 2

Esperase® is fermented according to U.S. Pat. No 3,723,250.

After fermentation, the broth is pretreated by addition of 1 l tap water/l broth, 35 g of $CaCl_2.2H_2O$/l broth, and 10 g of $Al_2(SO_4)_3$/l broth. The pH is constantly adjusted to 8.0 with aqueous sodium hydroxide during the $Al_2(SO_4)_3$ addition. The suspension is then flocculated by the addition of a cationic and an anionic flocculent: Superfloc C 521 (5 g/l broth) and Superfloc A 130 (300 mg/l broth).

Separation of the flocculated suspension is carried out by a centrifugation followed by a filtration in order to obtain a clear liquid. The filtrate is evaporated to a dry matter content corresponding to approx. 12% RI (refractive index) and heated to a temperature of approx. 37° C. At this temperature 250 g $Na_2SO_4$/l concentrate is added stepwise to the solution with rapid mixing. The pH is adjusted to 7.0 with sodium hydroxide and 20% acetic acid, and the suspension is mixed for 1/2 hour.

The precipitated enzyme is harvested on a filter press, and is redissolved in monopropylene glycol (2.5 l/kg filter cake) at 25° C. Undissolved material is removed by filtration, and the filter cake is flushed with a mixture of monopropylene glycol and water.

The Esperase® filtrate is diluted with water to a monopropylene glycol concentration of approx. 30%, the concentration of Esperase® being approx. 20 g/l.

The monopropylene glycol concentrate is subsequently treated with sodium aluminate (5 g/l) at pH 5.9 (adjusted with formic acid) and filtered. The filter cake is flushed with a mixture of monopropylene glycol and water.

The yield of Esperase® in this aluminate reaction is above 95%, and the colour reduction is above 80%.

I claim:

1. A method for purification of a desired enzyme from an impure protein solution, comprising the steps of:
   (a) simultaneously adding a soluble aluminate and an acid to an impure protein solution, wherein
      (i) the pH of the solution is maintained between 4–10;
      (ii) the pH is at least 1 pH unit from the isoelectric point of the enzyme to be purified;
      (iii) the amount of soluble aluminate added is between a maximum amount, which will precipitate no more than a negligible amount of enzyme and a minimal amount, which will leave no more than a negligible amount of impurities in solution; and
   (b) separating the supernatant containing the desired enzyme from the precipitate.

2. The method of claim 1, wherein step (a) further comprises addition of a water miscible solvent.

3. The method of claim 2, wherein the water miscible solvent is an alcohol.

4. The method of claim 3, wherein the alcohol is selected from the group consisting of a glycerol or a glycol.

5. The method of claim 3, wherein the alcohol is present in the mixture in an amount between 20 and 80% w/w.

6. The method of claim 1, wherein the acid is formic acid.

7. The method of claim 1, wherein pH is maintained between 5 and 8.

8. The method of claim 1, wherein the soluble aluminate is sodium aluminate.

9. The method of claim 1, wherein the maximum amount of aluminate is between 2 and 3% w/w of the solution, and that the minimal amount is between 0.3 and 1% w/w of the solution.

10. The method of claim 1, wherein the supernatant is separated from the precipitate by centrifugation or filtration.

11. The method of claim 1, wherein a flocculation agent is added after addition of the acid and the aluminate, but before the separation of the supernatant and the precipitate, and that the flocculation agent is a cationic flocculation agent.

12. The method of claim 1, wherein a flocculation agent is added after addition of the acid and the aluminate, but before the separation of the supernatant and the precipitate, and that the flocculation agent is an anionic flocculation agent.

* * * * *